United States Patent [19]

Studnicka et al.

[11] Patent Number: 5,171,875
[45] Date of Patent: Dec. 15, 1992

[54] BETA BRANCHED BORATE ESTERS

[75] Inventors: Noreen A. Studnicka, Pell Lake; J. Michael Clumpner, Delavan, both of Wis.; Anthony J. O'Lenick, Jr., Lilburn, Ga.

[73] Assignee: LCE Partnership, Lake Geneva, Wis.

[21] Appl. No.: 640,098

[22] Filed: Jan. 11, 1991

[51] Int. Cl.$^5$ ................................................. C07F 5/04
[52] U.S. Cl. ..................................... 558/296; 558/293; 558/297
[58] Field of Search ................. 558/293, 296, 295, 297

[56] References Cited

U.S. PATENT DOCUMENTS

| | | | |
|---|---|---|---|
| 3,454,617 | 7/1969 | Fischer | 260/462 |
| 3,660,459 | 5/1972 | Hughes | 260/469 |
| 3,723,495 | 3/1973 | Holtz | 260/462 |
| 4,731,190 | 3/1988 | O'Lenick | 252/49.3 |
| 4,800,077 | 1/1989 | O'Lenick | 424/70 |
| 4,830,769 | 5/1989 | O'Lenick | 252/49.3 |
| 5,080,834 | 1/1992 | Clumpner | 260/410.6 |

*Primary Examiner*—Howard T. Mars
*Assistant Examiner*—Margaret J. Page

[57] ABSTRACT

The present invention deals with the composition, and application of novel highly branched borate esters, which function as unique oil phases for use in personal care, textile and related applications. The properties of these novel compounds which makes them well suited for these applications is the fact that they are substantive to fibers, hair and skin, are very mild to the skin and eyes. These materials are surprisingly stable to hydrolysis.

11 Claims, No Drawings

BETA BRANCHED BORATE ESTERS

BACKGROUND OF THE INVENTION

Arts and Practices

Boric acid derivatives are known in the art. Boric acid esters are a class of compounds which conform to the following structure;

(RO)$_3$—B

There are a variety of methods of preparation of borate esters. The most common preparative method for boric acid esters is the reaction of boric acid with an alcohol. Low molecular weight alcohols are used in this process. The boric acid ester produced in the greatest quantity is methyl borate, used in the synthesis of sodium borohydride. The utilization relates to the hydrolytic instability of the ester and its reactivity to prepare the borohydride.

The most important references to other methods of preparation of borate esters are as follows;

U.S. Pat. No. 3,454,617 issued in 1969 to Fischer et al discloses a process for the preparation of borate esters of long chain aliphatic alcohols by oxidation of paraffins in the presence of boric acid. This method is not applicable to the compounds of the present invention since the critical guerbet alcohol portion of the molecule cannot be prepared by oxidation of paraffin. Additionally, there is no possibility to include alkylene oxide into the molecule using the Fischer technology.

U.S. Pat. No. 3,660,459 issued in 1972 to Hughes discloses that amino alcohols can be reacted with boric acid to make amino borates which can subsequently converted into quaternary ammonium compounds. These materials are useful as fabric softeners. These compounds are different from the compounds of the present invention in that they utilize amino alcohols, and do not recognize the importance of the guerbet functionality. Additionally, there is no possibility to include alkylene oxide into the molecule using this technology.

U.S. Pat. No. 3,723,495 issued in 1973 to Holtz discloses that unsaturated alcohols can be prepared by the reaction of triolefins with boron compounds followed by hydrolysis. These compounds are different from the compounds of the present invention in that they are alcohols. Not borate esters based upon guerbet alcohols. Additionally, there is no possibility to include alkylene oxide into the molecule using this technology. Borate esters of the prior art hydrolyze easily giving back the starting alcohol. This hydrolytic instability has significantly limited the utilization of these materials in many applications.

Guerbet alcohols, one raw material used in the preparation of the compounds of the present invention, are known to those skilled in the art. Many early patents dealt with the choice of catalyst for the preparation of the beta branched alcohol. Later patents dealt with compounds, compositions and processes which utilize the liquid nature of guerbet derivatives.

Several patents have issued which describe derivatives of guerbet alcohols. None of the patents describe in any way borate esters. All patents use the guerbet alcohol to obtain high molecular weight and liquidity in the products. Typical examples of such patents are;

U.S. Pat. No. 4,425,458 issued in 1984 to Lindner et al teaches that certain guerbet alcohol diesters are useful as plastic lubricants.

U.S. Pat. No. 4,731,190 issued in 1988 and U.S. Pat. No. 4,830,769 both issued to O'Lenick et al, and incorporated herein by reference, teaches that certain guerbet alcohol alkoxylates are useful as metal working lubricants.

U.S. Pat. No. 4,868,236 issued in 1989 to O'Lenick teaches that certain guerbet alcohol citrate esters are useful as plastic lubricants.

U.S. Pat. No. 4,800,077 issued in 1989 to O'Lenick et al, which is incorporated herein by reference, teaches that certain guerbet alcohol based quaternary compounds are useful liquid cosmetic and personal care compounds.

Oil soluble borate esters have been added to aircraft fuel because as they hydrolyze, boric acid results which inhibits the growth of microorganisms.

The compounds of the present invention, unlike other borate esters, are surprisingly stable to hydrolysis, lubricious, non irritating liquids which form films when applied to substrates like skin, hair and textile fibers.

THE INVENTION

The present invention deals with the composition, and application of novel highly branched borate esters, which are surprisingly hydrolytically stable and are oil phases for use in personal care, textile and related applications. The properties of these novel compounds which makes them well suited for these applications is the fact that they are substantive to fibers, hair and skin, are very mild to the skin and eyes.

A surprising feature of the compounds of the present invention is that a unique non greasy feel is obtained when the products of the present invention are applied to the skin. This makes the materials of the present invention very useful in personal care products. It is the use of beta branched alcohols like guerbet alcohols or aldol alcohols and their alkoxylates with their unique branching that results in the unique properties of these materials.

OBJECT OF THE INVENTION

It is the object of this invention to produce a high molecular weight borate ester that is highly lubricious, nonirritating, and stable to hydrolysis. The nature of these borate esters surprisingly relates to the fact that these borate esters are prepared from guerbet alcohols and their alkoxylates. The specific branching pattern, in addition to producing liquid derivatives also results in the desired stability to hydrolysis of these compounds. Additionally, the use of high molecular weight branched hydrophobic alcohols in the preparation of the compounds of the present invention results in products which are less irritating.

It is also an object of the present invention to provide a process of treating fiber which comprises contacting the fiber with an effective lubricating amount of the compounds of the invention.

The references cited herein are incorporated by reference to the extent applicable. Ratios and percentages are by weight and temperatures are Celsius unless otherwise stated.

DETAILED DESCRIPTION OF THE INVENTION

The compounds of the present invention are prepared by the reaction of the guerbet alcohol, or aldol alcohol or their alkoxylates with boric acid more specifically anhydrous boric acid.

Anhydrous boric acid, $B_2O_3$, is more properly called boric anhydrous. Other names include boron oxide, boron trioxide, or boron sesquioxide. It is a brittle, hygroscopic crystal.

Both types of alcohol from which the borate can be produced are highly regiospecifically beta branched. The difference is that one is dialkyl at the beta branch, the other is alkyl, alkylether branched.

Guerbet Alcohol (Dialkyl beta branched)
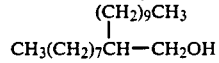

$$CH_3(CH_2)_7\overset{(CH_2)_9CH_3}{\underset{|}{CH}}-CH_2OH$$

Aldol Alcohol (Alkyl ether alkyl beta branched)

$$R'-\overset{R''}{\underset{|}{CH}}-CH_2-O-H$$

R' is alkyl 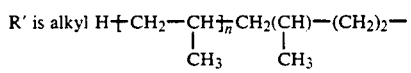

R'' is aklyl ether 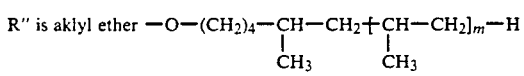

It will be understood by those skilled in the art that the above definition of R' and R'' will also include several other positional isomers.

Oxo alcohols, which have some methyl or other lower alkyl branch in the beta position are not suitable raw materials for the preparation of the compounds of the present invention. Oxo alcohols typically have between 20 and 30% methyl branching in the beta position. This is a consequence of the process used to make them. They lack the stability to hydrolysis exhibited by the higher alkyl and alkyl ether derivatives of the present invention. Additionally, they lack the lubricious properties and low irritation properties of the compounds of the present invention.

Aldol Alcohols used as raw materials in the preparation of compounds of the present invention are a new series of branched ether alcohols and their alkoxylates recently developed by Nova Molecular Technologies, Lake Geneva, Wis.

The alcohols, marketed under the trade name "Aldol Alcohol" and conform to the following structure;

ALDOL ALCOHOLS AND ALKOXYLATES $$R'-\overset{R''}{\underset{|}{CH}}-CH_2-O-(EO)_x-(PO)_y-(EO)_z-H$$

R' is 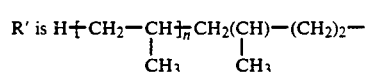

R'' is 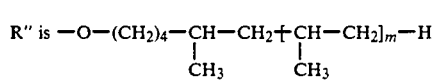

$R^3$ is lower alkyl;
EO is $-(CH_2CH_2-O)-$
PO is $-(CH_2CH(CH_3)-O)-$ x, y and z are independently integers from 0 to 20;
m is 1 or 2;
n is 1 or 2.

Guerbet Alcohols, the other type of beta branched alcohols useful as raw materials, have been known since the 1890's when Marcel Guerbet first synthesized these materials (M. Guerbet, C.R. Acad. Sci. Paris, 128, 511; 1002 (1899)). These materials are high in molecular weight and are liquid to very low temperatures. The guerbet reaction gives very specific branching in the alcohol as shown;

$$2ROH \longrightarrow R\overset{R}{\underset{|}{CH}}CH_2OH$$

As can be seen by the above reaction the molecules have substitution on the second carbon from the hydroxyl group. This branching has been found to be critical to the preparation of a product having the desired properties. If the branching were on the same carbon as the hydroxyl group, the hydroxyl group would be a secondary one and would be very hindered and has low reactivity. As one moves the branch position away from the beta carbon, the ability to liquefy under pressure, and condition to hair and fiber decreases.

Guerbet alcohols that are the reaction product of one specific raw material alcohol will result in a so called "homo-guerbet". In this case the product is symmetrical. If the starting alcohols used in the guerbet reaction are of differing molecular weights a so called "hetero-guerbet" results. This type of guerbet has a mixed distribution of all possible combinations of alcohols. For this reason R and R' in the generic formula may be the same or different.

$$R\overset{R'}{\underset{|}{C}}HCH_2OH$$
Heteroguerbet $$R\overset{R}{\underset{|}{C}}HCH_2OH$$
Homoguerbet The beta branched alcohol or alkoxylate is reacted with the boric acid under catalytic conditions to give the borate ester and water. The water is removed by distillation. Vacuum is used to drive the reaction to completion.

$$6ROH + B_2O_3 \xrightarrow[\text{catalyst}]{\text{heat}} 2B-(OR)_3 + 3H_2O$$

The reaction can be run without a catalyst. Catalysts are generally used at concentrations of between 0.05% to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titanates, organo tin compounds, organo zinc compounds, zinc oxide, magnesium oxide, calcium oxide, etc. Preferred is stannous oxylate. The reaction is conducted at between 140° and 240° C. under an inert nitrogen blanket. Preferred temperature range is between 180° and 210° C. Water is removed from the reaction which is done using a nitrogen sparge or vacuum of up to 10 mm.

Preferred Embodiments

In a preferred embodiment the sum of the carbon atoms in $R^2$ and $R^3$ ranges from 14 to 22. Within this range the maximum lubrication under pressure and the maximum lubricity is obtained. Compounds having lower values are not lubricious enough, and those with higher values do not exhibit the optimum lubrication properties. Most preferred values for the sum of the carbon atoms in $R^2$ and $R^3$ are 14 to 18.

In a preferred embodiment x, y and z are all zero. Another preferred embodiment x, y and z are each between 1 and 10.

The fibers which have been successfully treated with the compounds of the present invention are hair and textile fiber. The preferred textile fibers are cotton and polyester.

The preferred concentration of compound to obtain the desired lubricating effect is between 0.01 and 25%. More commonly the concentration ranges from 0.1 to 5%.

EXAMPLES

EXAMPLES OF GUERBET ALCOHOL

The preparation of guerbet alcohols is a process known to those skilled in the art. The reaction is conducted commercially by several companies including Exxon Chemical, Henkel Corporation, Condie Cheime, and Alkaril Chemicals. Guerbet alcohols are alkoxylated using processes known to those skilled in the art and are available from Nova Molecular Technologies. Guerbet Alcohols conform to the following structure

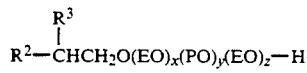

$R^2$ is alkyl having from 4 to 24 carbon atoms;
$R^3$ is alkyl having from 4 to 24 carbon atoms;
EO is $-(CH_2CH_2-O-)-$;
PO is $-(CH_2CH(CH_3)-O-)-$;
x, y, and z are independently integers each ranging from 0 to 20.

| Example | $R^3$ | $R^2$ | x | y | z |
|---|---|---|---|---|---|
| 1 | $C_8H_{17}$ | $C_{10}H_{21}$ | 0 | 0 | 0 |
| 2 | $C_8H_{17}$ | $C_{10}H_{21}$ | 5 | 5 | 5 |
| 3 | $C_8H_{17}$ | $C_{10}H_{21}$ | 20 | 10 | 20 |
| 4 | $C_{10}H_{21}$ | $C_{12}H_{23}$ | 1 | 10 | 5 |
| 5 | $C_{10}H_{21}$ | $C_{12}H_{23}$ | 0 | 0 | 0 |
| 6 | $C_{10}H_{21}$ | $C_{12}H_{23}$ | 5 | 5 | 5 |
| 7 | $C_{10}H_{21}$ | $C_{12}H_{23}$ | 10 | 10 | 10 |
| 8 | $C_7H_{15}$ | $C_5H_{11}$ | 3 | 10 | 0 |
| 9 | $C_7H_{15}$ | $C_5H_{11}$ | 0 | 0 | 0 |
| 10 | $C_{18}H_{37}$ | $C_{16}H_{33}$ | 10 | 10 | 10 |
| 11 | $C_{18}H_{37}$ | $C_{16}H_{33}$ | 5 | 5 | 4 |
| 12 | $C_{18}H_{37}$ | $C_{16}H_{33}$ | 0 | 5 | 12 |
| 13 | $C_{10}H_{21}$ | $C_{10}H_{21}$ | 1 | 0 | 6 |
| 14 | $C_{10}H_{21}$ | $C_{10}H_{21}$ | 20 | 3 | 14 |
| 15 | $C_8H_{17}$ | $C_8H_{17}$ | 5 | 1 | 0 |
| 16 | $C_8H_{17}$ | $C_8H_{17}$ | 0 | 0 | 0 |

Examples of Aldol Alcohols

The following aldol alcohols are available from Nova Molecular Technologies, Lake Geneva, Wis.;

| Example | Name | n | m | x | y | z |
|---|---|---|---|---|---|---|
| 17 | ALDOL ALCOHOL 21 | 1 | 1 | 0 | 0 | 0 |
| 18 | ALDOL ALCOHOL 27 | 2 | 2 | 0 | 0 | 0 |
| 19 | ALDOL ALCOHOL 21-E3 | 1 | 1 | 3 | 0 | 0 |
| 20 | ALDOL ALCOHOL 21-E5 | 1 | 1 | 5 | 0 | 0 |
| 21 | ALDOL ALCOHOL 21-E15 | 1 | 1 | 15 | 0 | 0 |
| 22 | ALDOL ALCOHOL 21-E20 | 1 | 1 | 20 | 0 | 0 |
| 23 | ALDOL ALCOHOL 27-P20-E20 | 2 | 2 | 0 | 20 | 20 |
| 24 | ALDOL ALCOHOL 27-E10-P10 | 2 | 2 | 10 | 10 | 0 |
| 25 | ALDOL ALCOHOL 27-E5-P4 | 2 | 2 | 5 | 4 | 0 |
| 26 | ALDOL ALCOHOL 27-E20 | 2 | 2 | 20 | 0 | 0 |

Boric Acid Reactions

EXAMPLES 27-52

To the specified amount of the specified guerbet alcohol, aldol alcohol or guerbet alcohol alkoxylate, aldol alcohol alkoxylate is added the specified number of grams boric acid and 2.0 grams of stannous oxylate (Fascat 2001). The temperature is then increased to 160°-200° C., under nitrogen sparge. By-product water begins to distill off. Vacuum is applied to keep the water distilling. When 97% of the theoretical water is removed the reaction is cooled. The desired product is obtained without and additional purification.

| | Guerbet Reactant | | Boric Acid | Catalyst | |
|---|---|---|---|---|---|
| Example | Example | Grams | Grams | Type | Grams |
| 27 | Examp. 1 | 244.0 | 116.4 | | None |
| 28 | Examp. 2 | 979.0 | 116.4 | | None |
| 29 | Examp. 3 | 3428.0 | 116.4 | | None |
| 30 | Examp. 4 | 1206.0 | 116.4 | | None |
| 31 | Examp. 5 | 308.0 | 116.4 | | None |
| 32 | Examp. 6 | 892.0 | 116.4 | | None |
| 33 | Examp. 7 | 1778.0 | 116.4 | | None |
| 34 | Examp. 8 | 904.0 | 116.4 | | None |
| 35 | Examp. 9 | 182.0 | 116.4 | | None |
| 36 | Examp. 10 | 1948.0 | 116.4 | B | 12.0 |
| 37 | Examp. 11 | 1169.0 | 116.4 | B | 10.0 |
| 38 | Examp. 12 | 2074.0 | 116.4 | B | 12.0 |
| 39 | Examp. 13 | 590.0 | 116.4 | B | 2.0 |
| 40 | Examp. 14 | 1955.0 | 116.4 | B | 1.0 |
| 41 | Examp. 15 | 485.0 | 116.4 | B | 0.5 |
| 42 | Examp. 16 | 206.0 | 116.4 | C | 12.0 |
| 43 | Examp. 17 | 294.0 | 116.4 | A | 12.0 |
| 44 | Examp. 18 | 378.0 | 116.4 | A | 2.0 |
| 45 | Examp. 19 | 426.0 | 116.4 | A | 12.0 |
| 46 | Examp. 20 | 514.0 | 116.4 | A | 12.0 |
| 47 | Examp. 21 | 954.0 | 116.4 | A | 2.0 |
| 48 | Examp. 22 | 1174.0 | 116.4 | A | 0.9 |
| 49 | Examp. 23 | 2438.0 | 116.4 | A | 12.0 |
| 50 | Examp. 24 | 1408.0 | 116.4 | A | 8.0 |
| 51 | Examp. 25 | 836.0 | 116.4 | | None |
| 52 | Examp. 26 | 1256.0 | 116.4 | B | 12.0 |

Catalysts
A is stannous oxylate (Fascat from ATO Chem)
B is an organo titanate (Tyzor from DuPonte)
C is para toluene sulfonic acid

HYDROLYTIC STABILITY

Compounds of The Present Invention

% Hydrolysis 1 gram in 60 C

-continued

| Example Number | water for 24 hrs. |
| --- | --- |
| 27 | 1.2 |
| 31 | 2.0 |
| 35 | 0.8 |
| 42 | 0.9 |
| 43 | 1.1 |
| 44 | 1.0 |

Comparative Compounds

| Compound Name | % Hydrolysis 1 gram in 60 C water for 24 hrs. |
| --- | --- |
| Tridecyl borate (Derived from decyl alcohol) | 95.3 |
| Trilauryl borate (Derived from lauryl alcohol) | 97.6 |
| Trimethyl borate (Derived from methanol) | 100.0 |

As can be easily seen from the above data the compounds of the present invention have outstanding hydrolytic stability.

What is claimed:

1. A borate ester prepared by the esterification reaction of boric acid with an alcohol or alcohol alkoxylate selected from the group consisting of
   (a) a guerbet alcohol or alcohol alkoxylate of the formula;

$$R^2-\overset{R^3}{\underset{|}{C}}HCH_2O-(EO)_x(PO)_y(EO)_z-H$$

wherein;
$R^2$ is alkyl having from 7 to 18 carbon atoms;
$R^3$ is alkyl having from 7 to 18 carbon atoms;
EO is $-(CH_2CH_2-O)-$;
PO is $-(CH_2CH(CH_3)-O)-$;
x,y,z are independently integers each ranging from 0 to 20;
and
(b) an aldol alcohol or aldol alcohol alkoxylate is of the formula;

$$R'-\overset{R''}{\underset{|}{C}}H-CH_2-O-(EO)_x-(PO)_y-(EO)_z-H$$

wherein;

R' is 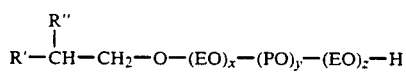

R'' is 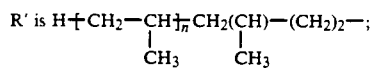

EO is $-(CH_2CH_2-O)-$;
PO is $-(CH_2CH(CH_3)-O)-$;
x, y and z are independently integers from 0 to 20;
m is 1 or 2;
n is 1 or 2;
said esterification reaction is carried out by reacting said guerbet alcohol or guerbet alcohol alkoxylate, aldol alcohol or aldol alcohol alkoxylate with said boric acid at a temperature of between 140°-240° C.

2. The borate ester of claim 1 wherein said alcohol or alcohol alkoxylate is of the formula;

R' is 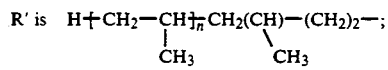

R'' is 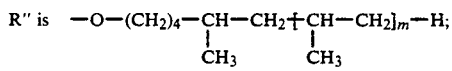

EO is $-(CH_2CH_2-O)-$;
PO is $-(CH_2CH(CH_3)-O)-$;
x, y and z are independently integers from 0 to 20;
m is 1 or 2;
n is 1 or 2.

3. The borate ester of claim 1 wherein said alcohol or alcohol alkoxylate is of the formula;

$$R^2-\overset{R^3}{\underset{|}{C}}HCH_2O-(EO)_x(PO)_y(EO)_z-H$$

wherein;
$R^2$ is alkyl having from 7 to 18 carbon atoms;
$R^3$ is alkyl having from 7 to 18 carbon atoms;
EO is $-(CH_2CH_2-O)-$;
PO is $-(CH_2CH(CH_3)-O)-$;
x,y,z are integers each independently ranging from 0 to 20;

4. The borate ester of claim 2 wherein x, y and z are independently integers ranging from 0 to 10.

5. The borate ester of claim 2 wherein x, y and z are all zero.

6. The borate ester of claim 2 wherein x is 5, y is 0 and z is 0.

7. The borate ester of claim 2 wherein x is 0, y is 15 and z is 0.

8. The borate ester of claim 3 wherein x, y and z are independently integers ranging from 0 to 10.

9. The borate ester of claim 3 wherein x, y and z are all zero.

10. The borate ester of claim 3 wherein x is 5, y is 0 and z is 0.

11. The borate ester of claim 3 wherein x is 0, y is 15 and z is 0.

* * * * *